(12) United States Patent
Petzold et al.

(10) Patent No.: US 7,038,765 B2
(45) Date of Patent: May 2, 2006

(54) METHOD OF OPTICALLY MEASURING BLACK CARBON IN THE ATMOSPHERE AND APPARATUS FOR CARRYING OUT THE METHOD

(75) Inventors: Andreas Petzold, München (DE); Markus Schönlinner, Waging (DE)

(73) Assignees: Deutsches Zentrum für Luft- und Raumfahet e.V., Köln (DE); ESM Andersen Instruments GmbH, Erlangen (DE)

( * ) Notice: Subject to any disclaimer, the term of this patent is extended or adjusted under 35 U.S.C. 154(b) by 350 days.

(21) Appl. No.: 10/646,964

(22) Filed: Aug. 22, 2003

(65) Prior Publication Data

US 2004/0156036 A1    Aug. 12, 2004

(30) Foreign Application Priority Data

Aug. 28, 2002    (DE) ................................. 102 40 204

(51) Int. Cl.
*G01N 1/00* (2006.01)
*G01N 21/00* (2006.01)

(52) U.S. Cl. ..................... 356/38; 356/446; 356/437
(58) Field of Classification Search ........ 356/432–440, 356/38, 446
See application file for complete search history.

(56) References Cited

U.S. PATENT DOCUMENTS

| | | | |
|---|---|---|---|
| 3,790,286 A * | 2/1974 | Kraus .......................... | 356/369 |
| 4,093,705 A * | 6/1978 | Kraus et al. ................. | 423/450 |
| 4,893,934 A | 1/1990 | Hansen | |
| 5,373,367 A | 12/1994 | DeGunther et al. | |
| 5,751,416 A * | 5/1998 | Singh et al. ................. | 356/311 |
| 6,570,655 B1 | 5/2003 | Schiefer et al. | |
| 6,662,627 B1 * | 12/2003 | Arnott et al. ............... | 73/24.02 |
| 6,775,004 B1 * | 8/2004 | Putman ....................... | 356/445 |

FOREIGN PATENT DOCUMENTS

| | | |
|---|---|---|
| DE | 197 35 205 | 2/1999 |
| DE | 100 57 652 | 6/2001 |
| EP | 0902273 A2 * | 11/1999 |

OTHER PUBLICATIONS

Petzold , A. and H. Kramer, "An improved aerosol absorption photometer for the determination of black carbon in ambient air", Journal of Aerosol Science, 32 pp. 37-38, 2001.

Radiation Budget of the Boundary Layer Part II: Simultaneous Measurement of Mean Solar Volume Absorption and Extinction Coefficients of Particles, by Gottfried Hänel, Beitr. Phys. Atmosph. vol. 60, No. 2, May 1987 (pp. 241-247).

* cited by examiner

*Primary Examiner*—Hoa Q. Pham
(74) *Attorney, Agent, or Firm*—Collard & Roe, P.C.

(57) ABSTRACT

For optically measuring black carbon in the atmosphere an aerosol particle collection area of a filter tape is continually illuminated by an illumination source with light of one or more wavelengths. Transmitted and reflected light fractions are measured at several precisely defined angles or angle ranges, such as of 0°, 120 to 140° and 165° to 180° by photodetectors arranged correspondingly relative to the illumination source, achieving maximum symmetry for the angles to be measured. The loading of the filter tape collection area with light absorbing aerosol material is continually determined from the change in the optical properties of the collection area with the aid of known algorithms from transmissivities and reflectivities as detected.

9 Claims, 6 Drawing Sheets

METHOD OF OPTICALLY MEASURING BLACK CARBON IN THE ATMOSPHERE AND APPARATUS FOR CARRYING OUT THE METHOD

FIELD OF THE INVENTION

The invention relates to a method of optically measuring black carbon in the atmosphere and an apparatus for carrying out the method.

PRIOR ART

Black carbon (soot) is a leading component in particulate emissions from an incomplete combustion process. The German Standard hitherto for measuring black carbon in the air is VDI 2465 Sheet ½. The guideline requirements define thermal methods as a reference for immission measurements of black carbon, with the aid of which daily or weekly filter data is analyzed. This, however, fails to make it possible to furnish the measuring data resolved in time/on a daily basis.

For optically measuring black carbon the ambient aerosol is deposited on a single filter or filter tape. The change in the optical properties of the particle-loaded filter matrix as compared to a particle-free matrix is determined either in transmission (ATN) or in reflexion (REF). The change in the blackening of the filter due to particle loading is an indication of the mass loading of absorbing material by application of a simple relationship derived from the Lambert-Beer law $$ATN = -100\ln\frac{T}{T_0} = \sigma_{ATN} S_{BC} \tag{1a}$$

$$REF = -100\ln\frac{R}{R_0} = 2\sigma_{REF} S_{BC} \tag{1b}$$

where T, $T_0$ and R, $R_0$ stand for the transmittance and reflectance respectively of the filter matrix as particle-loaded (no index) and particle-free (index 0). $S_{BC}$ designates the loading of the filter with black carbon specific to the surface area of the collection area (in $\mu gcm^{-2}$), $\sigma_{ATN}$ and $\sigma_{REF}$ are the proportionality factors between filter loading $S_{BC}$ and the attenuation of the light due to particle-loading in transmitted light ($\sigma_{ATN}$) and in reflected light ($\sigma_{REF}$). Multiple scattering effects in aerosol or between particles and filter matrix are neglected.

U.S. Pat. No. 4,893,934 describes an aethalometer comprising a light source and a sole light detector as well as two light paths from the light source to the light detector. A quartz fibre filter is also provided whose collection area is located in the one light path, whilst the other light path serves as the reference area. Through the collection area of the filter ambient air is directed so that aerosol particles are able to be deposited on the filter.

In the housing of the aethalometer a rotating disk is provided with an opening so that light from the light source passes alternately through the two light paths. The output voltage of the detector located beneath the filter is applied to a voltage-controlled oscillator (VCO). The pulses for determining the light transmission passing separately through the two light paths are counted and compared, from which the absorption coefficient of the deposited aerosol particles is determined.

In the known aethalometer the particles are deposited on a filter or filter tape to thus permit determining the mass concentration of the black carbon over a longer period of time, up to several months depending on the concentration. Since in this known aethalometer multiple scattering effects as per equation (1a) are neglected, the mass concentration of the black carbon as established by the system employed depends on the light-scattering aerosol components. This cross-sensitivity may result in the measured values being seriously falsified. Apart from this, the air intake is unsuitable for larger particle diameters.

For determining the black carbon content of atmospheric aerosol samples an optical assembly was presented permitting simultaneous measurement of transmitted and reflected radiation (see: Petzold, A. and H. Kramer, "An improved aerosol absorption photometer for the determination of black carbon in ambient air", Journal of Aerosol Science, 32, pages 37–38, 2001). In this assembly aerosols are deposited on a filter tape and the collection area of the aerosol particles is illuminated with an LED. Photodetectors are arranged both in the area between the photodiode serving as the illumination source and the filter tape and beneath the filter tape so that both the transmitted light fractions as well as the light fractions reflected by the filter tape can be simultaneously measured.

SUMMARY OF THE INVENTION

The object of the invention is to improve the measurement and thus the determination of transmitted and reflected light fractions to achieve an enhanced signal average over an extended area.

In accordance with the present invention this and other objects can be achieved by a method of optically measuring black carbon in the atmosphere, comprising the steps of depositing aerosols from a stream of air onto a filter tape; illuminating an aerosol particle collection area of said filter tape continually by an illumination source with light of one or more wavelengths; measuring simultaneously light fractions both transmitted through and reflected from said filter tape at several precisely defined angles/angle ranges by means of photodetectors arranged correspondingly relative to said illumination source in achieving maximum symmetry for the angles to be measured, and determining continually the loading of said filter tape collection area with light-absorbing aerosol material from the change in the optical properties of said collection area caused by said loading with the aid of known algorithms from transmissivities and reflectivities as detected.

In accordance with the invention for measuring the transmitted and reflected light fractions the photodetectors are arranged opposite each other at precisely defined angles or angle ranges of 0°, 120° to 140° and from 165° to 180° preferably in ring-shaped mounting devices arranged concentrically to the optical axis of the at least one illumination source. The resulting maximum symmetry in the multiple angle measurement assembly in accordance with the invention for the angle ranges to be measured enhances a signal average over an expansive filter area for a highly compact structure of a measuring apparatus in the form of a measuring head.

To reduce scattered light the ring-shaped mounting devices in which the photodetectors are mounted opposite each other are preferably defined in two different planes.

Instead of a reference path as provided in the known aethalometer, for example, in accordance with the invention the light intensity of the illumination source is continually measured by assigning a photodetector to the illumination source.

Furthermore, a dusting passage is configured in the measuring head to ensure continual dusting of the filter tape and via which also larger particles (>10 μm) can gain access to the filter tape. In addition, for grading the size of the particles an external pre-separator may be arranged upstream of the dusting passage.

When measuring with light of a single wavelength only a narrow-band light source, such as a color LED is employed. When making the measurement with several wavelengths a wideband light source is used and a bandpass filter is arranged upstream of the individual detectors.

BRIEF DESCRIPTION OF THE DRAWINGS

The invention will now be detailed with reference to the drawings in which.

DETAILED DESCRIPTION

Figure 1:
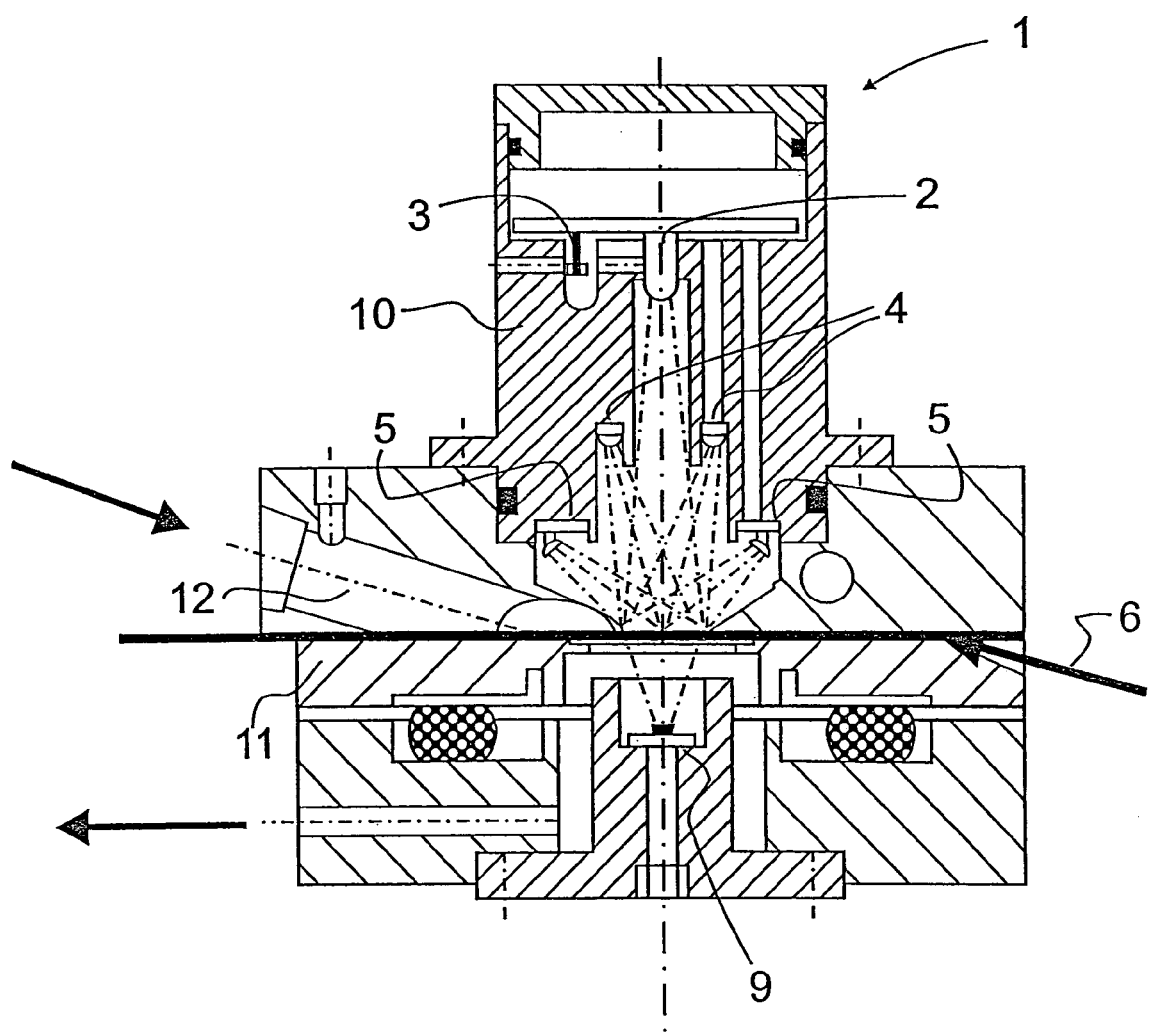
FIG. 1 is a vertical section view of one embodiment of an apparatus in the form of a measuring head for a single wavelength.

Referring to FIG. 1 there is illustrated diagrammatically an apparatus in the form of a measuring head 1. Provided in the upper housing part 10 of the measuring head 1 is a LED 2 having a wavelength of, for example, λ=670 nm as an illumination source. For monitoring the light intensity a photodetector 3 is assigned to the LED 2. In the middle portion of the upper housing part 10, two photodetectors 4 and, somewhat lower, two further photodetectors 5 are provided for measuring the backscattered (reflected) radiation.

Provided between the upper housing part 10 and a lower housing part 11 is a filter tape 6 indicated by the bold line. Arranged in the lower housing part 11 beneath the filter tape 6 is a further photodetector 9 for measuring or detecting transmitted radiation. Furthermore, in the lower portion of the upper housing part 10 there is provided a dusting passage 12 configured so that continual dusting of the filter tape 6 is assured.

Figure 2:
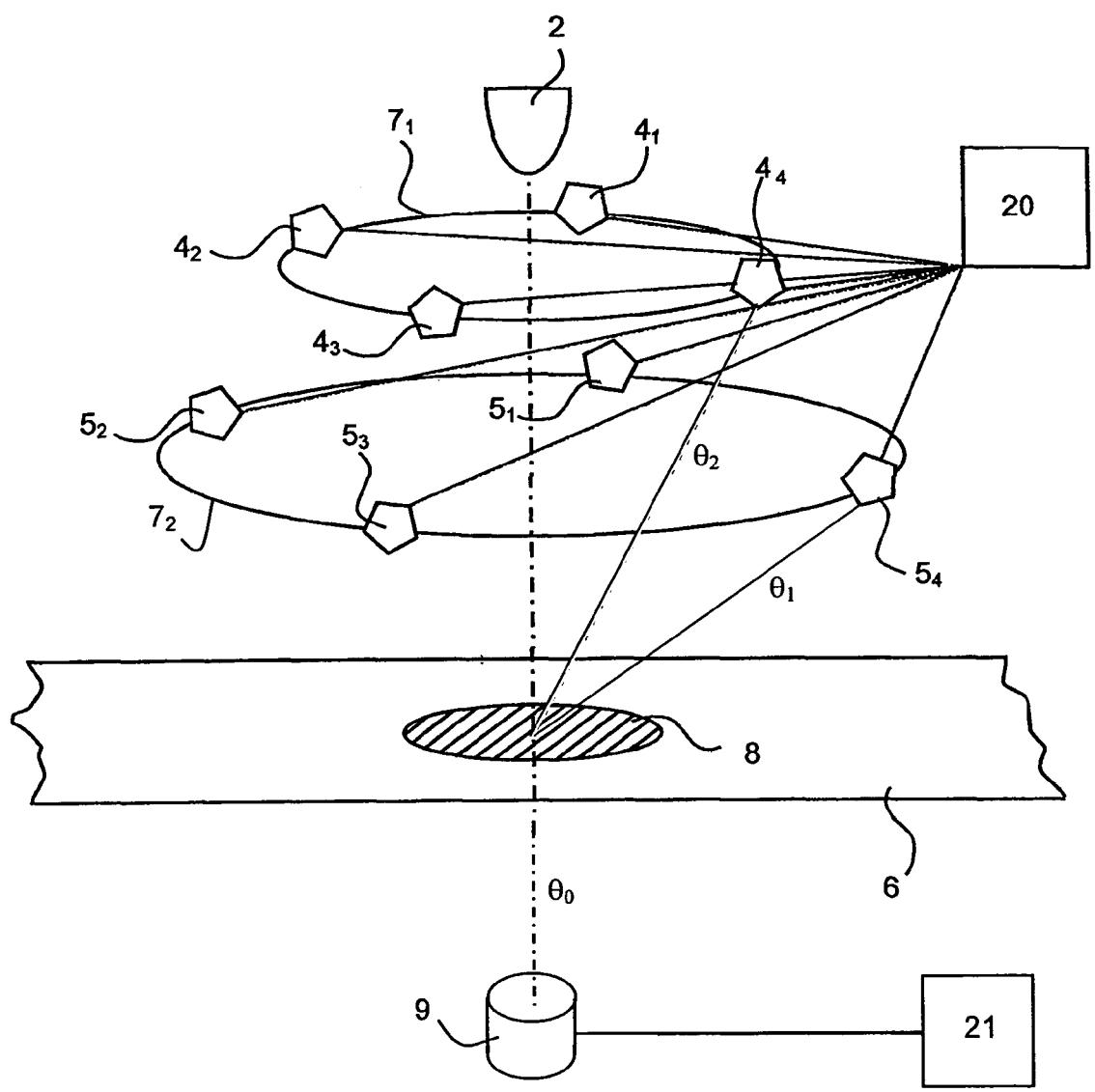
FIG. 2 is a greatly simplified perspective representation of a measuring assembly.

Referring now to FIG. 2 there is illustrated in a greatly simplified perspective representation how four photodetectors $4_1$ to $4_4$ are provided on a first ring-shaped mounting device $7_1$ preferably equispaced angularly from each other below the illumination source in the form of the LED 2 for detecting the backscatted radiation whilst somewhat further down on a second ring-shaped mounting device $7_2$ likewise four photodetectors $5_1$ to $5_4$ are provided.

An aerosol particle-laden collection area 8 on the filter tape 6 is evident from FIG. 2. Beneath the filter tape 6 there is provided the photodetector 9 for transmitted radiation. In the perspective representation, the angles relating to the reflected radiation, i.e. the angles θ=0°; $θ_1$=130° and $θ_2$=165° are entered.

Arranged opposite each other in the two ring-shaped mounting devices $7_1$ and $7_2$ in all cases are two photodetectors, for example, in the first ring-shaped mounting device $7_1$, the photodetectors $4_1$ and $4_3$ respectively $4_2$ and $4_4$ as well as in the second ring-shaped mounting device $7_2$ arranged lower down the photodetectors $5_1$ and $5_3$ respectively $5_2$ and $5_4$. As evident from FIG. 2 the ring-shaped mounting devices $7_1$ and $7_2$ are arranged concentrically to the optical axis of the measuring head 1 indicated dot-dashed.

By reason of this arrangement of the photodetectors 4 and 5 respectively each in the form of detectors arranged opposite each other, a maximum symmetry with respect to the angle measuring assembly for the angle ranges to be measured is achieved in regards to the illumination source in the form of LED 2. With a highly compact configuration of the measuring head, a better signal average over the extended collection area 8 on the filter tape 6 is attained.

Figure 3:
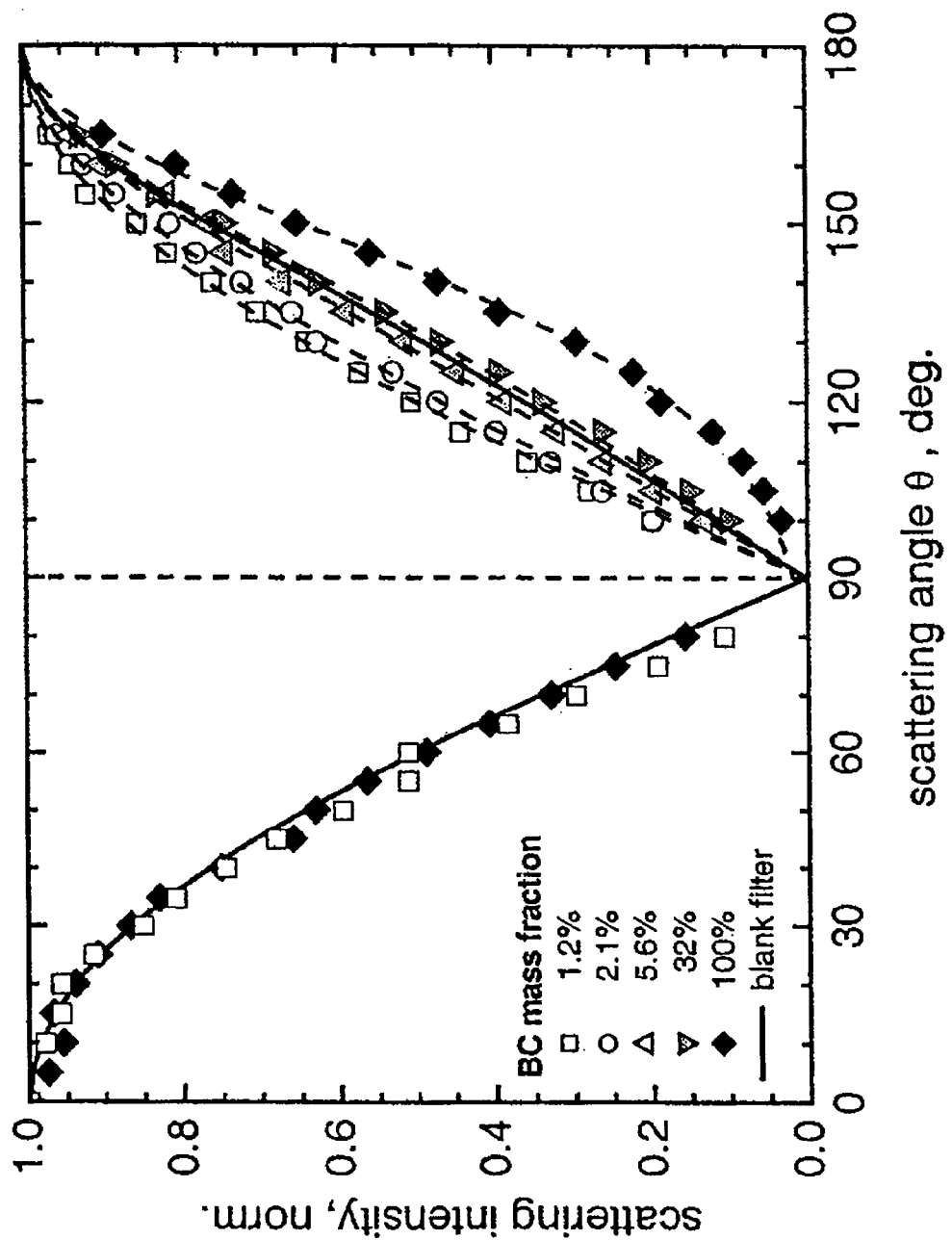
FIG. 3 is a diagram showing the angular distribution of radiation scattered in the two half-spaces as in dependence on the composition of the aerosol.

The optimum position of the photodetectors 4, 5 for detecting the radiation transmitted and reflected as a whole was derived from the analysis of the angle distribution of the loaded filter. This analysis showed that the angle distributions can be represented by a linear combination of a fraction of a diffusely scattered radiation and a fraction of radiation reflected at a rough surface. The parameterized angle distributions can be represented as $$S(\theta) = I\cos\theta \qquad (2a)$$
(for the front half-space, $\theta = 0 - 90°$)
and $$S(\theta) = I\left(\alpha\cos(\theta - 180°) + (1 - \alpha)\exp\left[-\frac{1}{2}\frac{(\theta - 180°)^2}{\sigma^2}\right]\right) \qquad (2b)$$
(for the rear half-space, $\theta = 90 - 180°$)

where α is the fraction of the diffusely scattered radiation and σ the roughness of the filter surface (see also FIG. 3).

Referring to FIG. 3 there is illustrated the angle distribution of the radiation scattered in the front half-space, θ=0–90° and in the rear half-space, θ=90–180° dependent on the composition of the aerosol. Hereby, the composition of the aerosol is entered as a fraction of the light absorbing components of the black carbon (BC) in the mass as a whole. In this graph the scattering angle θ in degrees is entered on the abscissa and the normalized scattering intensity is entered on the ordinate.

Figure 4:
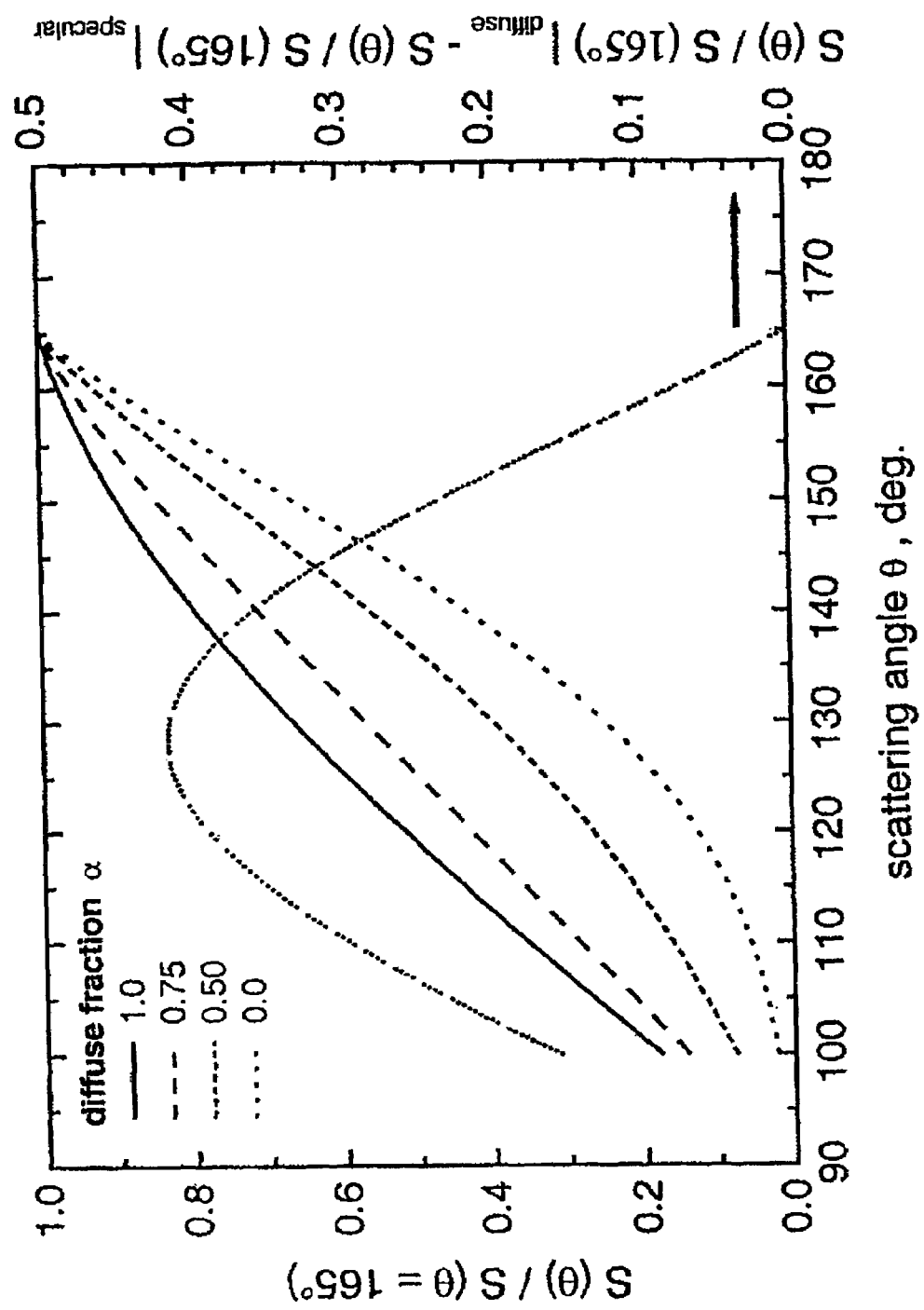
FIG. 4 is a graphic representation of the ratio of the signals relating to the various angles of observation θ.

The positioning of a detector with $θ_1$=130° permits distinguishing diffusely scattered radiation from reflected radiation with maximum resolution. (See FIG. 4) Entered on the left-hand axis/ordinate is the ratio of the signals for angles of observation θ and θ=165° as a function of the diffuse fraction of the scattered radiation and on the right-hand Y axis/ordinate the difference of the signal ratios for totally diffuse and totally reflected radiation as a function of the angle of observation θ.

Figure 5:
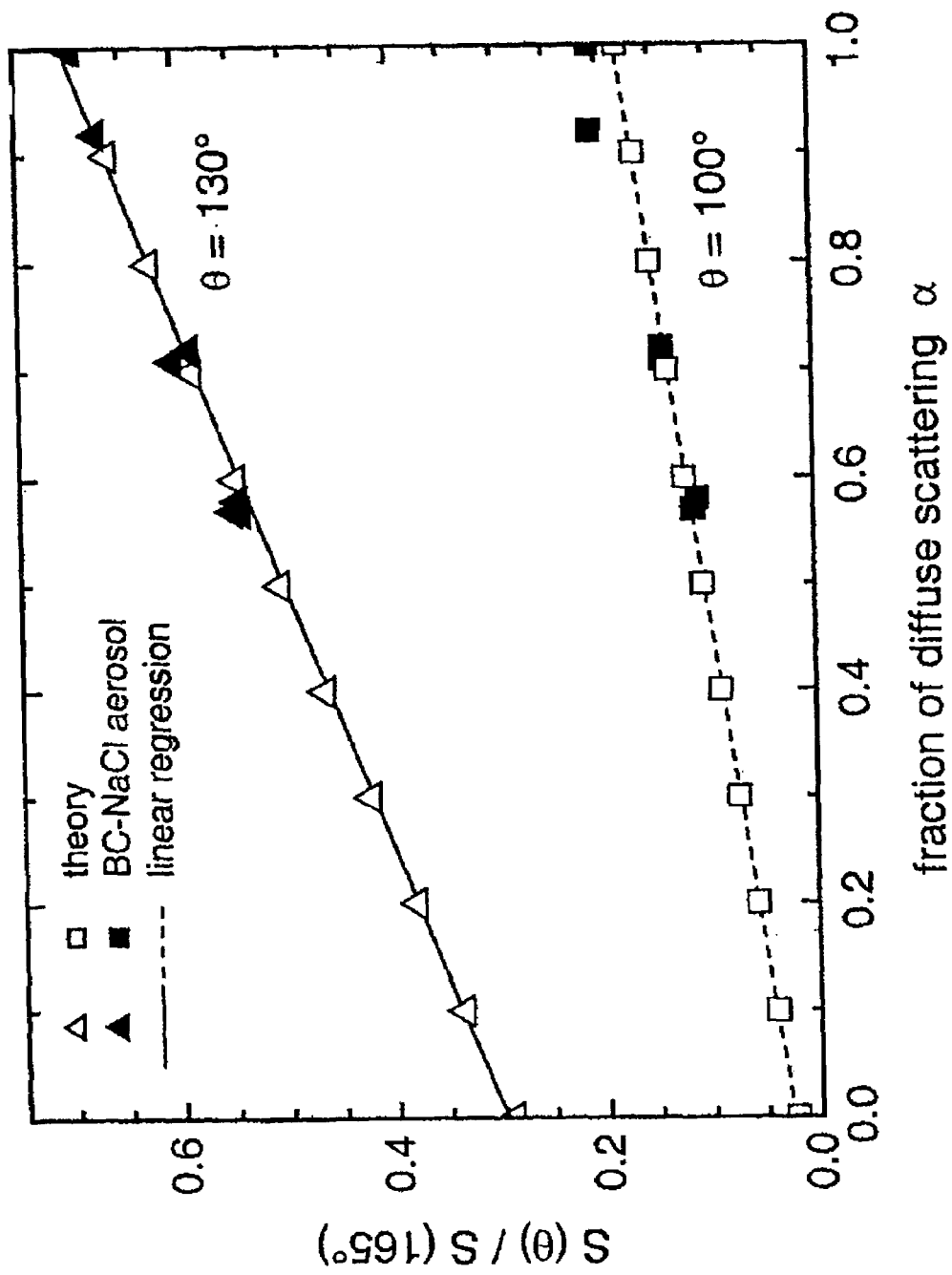
FIG. 5 is a graphic representation of a signal ratio of detectors at angles of observation θ=130° and 100° dependent on the fraction of diffuse scattering radiation.

The relation between the measured signal ratio $S(θ_1)/S(θ_2)$ and the diffuse fraction of the backscattered radiation is linear. (See FIG. 5) Entered in FIG. 5 is the signal ratio of the detectors at the angles of observation 130° and 100° in relation to an angle of 165° in dependence on the fraction of diffuse scattering with the fraction α of diffuse scattering on the abscissa and the ratio $S(\theta)/S(165°)$ on the ordinate.

This thus permits definitely obtaining the diffuse scattered fraction α from the signal ratio as measured. Having determined the parameter α then permits in conclusion calculating the total radiation scattered in the rear half-space from equation (2b). To obtain the transmitted radiation in the front half-space from equation (1) a measurement at θ=0° suffices.

The total intensities as thus obtained are, for the front half-space, $$I_t = \int_{-90°}^{90°} S(\theta = 0°)\cos\theta \, d\theta = 2S(\theta = 0°) \quad (3)$$

and, for the rear half-space, $$I_t = \alpha \int_{90°}^{270°} S(\theta = 180°)\cos(\theta - 180°) \, d\theta +$$
$$(1-\alpha) \int_{90°}^{270°} S(\theta = 180°)\exp\left[-\frac{1}{2}\frac{(\theta - 180°)^2}{\sigma^2}\right] d\theta$$
$$= S(\theta = 180°)\left(2\alpha + (1-\alpha)\sqrt{2\pi}\,\sigma\right) \quad (4)$$

From these radiation intensities, the light absorption caused by the deposited particles is determined via a known algorithm (see Hänel G., Radiation budget of the boundary layer, Part II, Simultaneous measurement of mean solar volume absorption and extinction coefficient of particles, Phys. Atmosph., 60, 241–247, 1987).

As a result, this algorithm furnishes the optical density $\tau_L$ of the filter loaded with the particles and the ratio $SSA_L$ of the light scattering to light extinction (single scattering albedo) of the loaded filter. It is from these parameters that in conclusion the mass loading of the filter with light-absorbing aerosol $S_{BC}$ is determined via $$ABS = 100(1 - SSA_L)\tau_L = \sigma_{ABS} S_{BC} \quad (5)$$

The parameter $\sigma_{ABS}$ can be obtained from calibrating the method against a chemical method of measuring the black carbon (e.g. VDI 2465, Part 1) in the aerosol.

APPLICATION EXAMPLE

The described method was put to use in determining the black carbon content in a mixture of light-scattering carbon). The mass percentage of the black carbon varied between 1% and 100%. In an ideal method the change in the optical filter properties (transmissivity, equation (1a), reflectivity, equation (1b), absorptance, equation (5)) caused by the particle loading of the filter is directly proportional to the loading of the filter with black carbon and is thus represented by an originating straight line.

Figure 6:
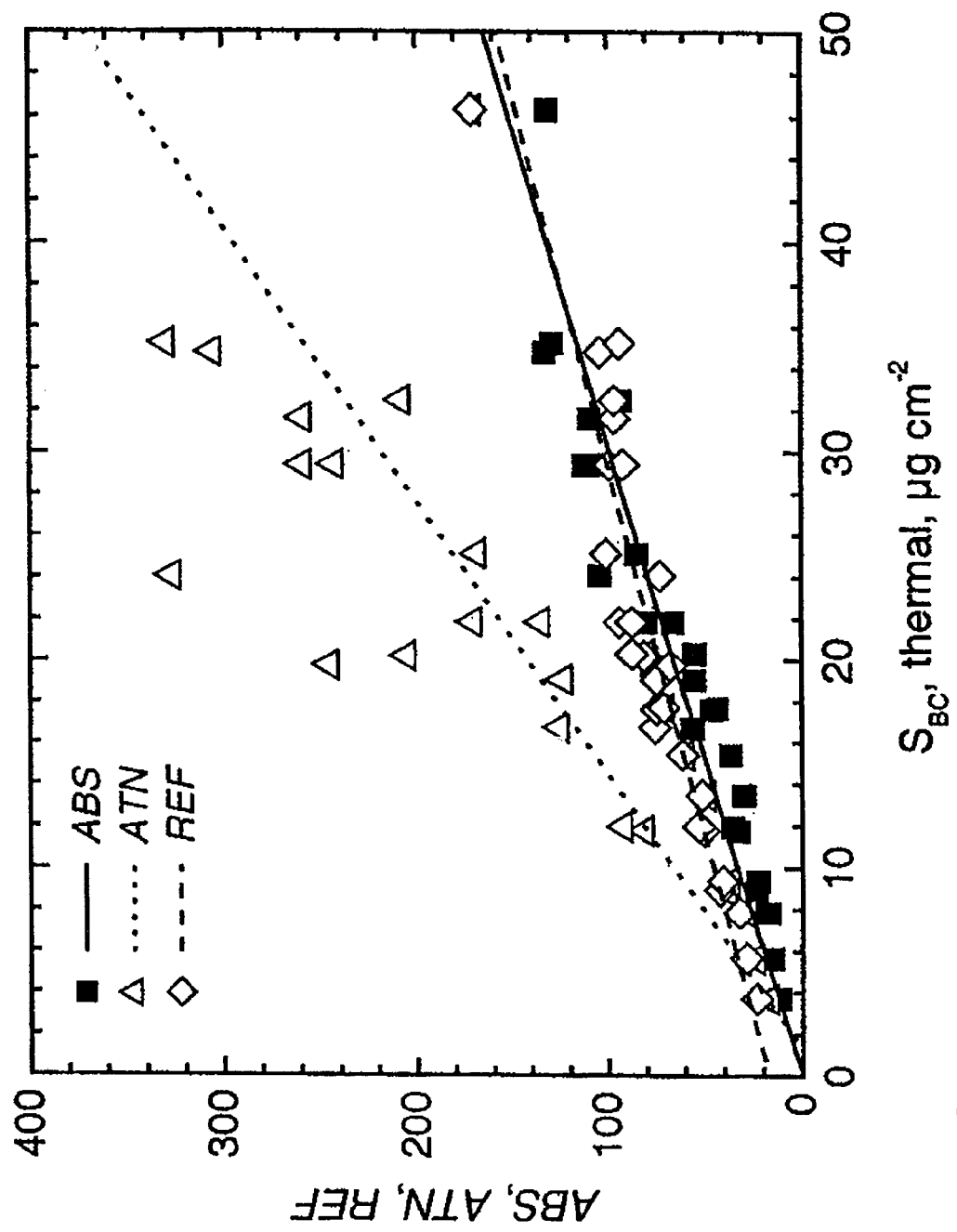
FIG. 6 is a graphic representation of the measured values ATN (transmission), REF (reflection) and ABS (multiple angle absorption measurement) of a measured loading of the filter with black carbon as measured.

FIG. 6 shows the relationship between the measured values ATN, REF and ABS and the loading of the filter with black carbon as measured independently in accordance with VDI 2465, Sheet 1, i.e. for a transmission measurement (ATN), reflectivity measurement (REF) and for the method as described (ABS).

Table 1 lists the corresponding results of the correlation analysis. The multiple angle absorption measurement as described above thus exhibits high correlation for simultaneously zero crossover of the regression straight lines. Current prior art methods exhibit either a strong scattering in the measured values (transmission) or an intercept in a significant departure from zero (reflectivity). This thus documents the improvement, as anticipated, in determining the black carbon in the air by the multiple angle absorption measurement as described.

A correlation analysis of the relation between the measured value of the transmission measurement (ATN), reflectivity measurement (REF) and multiple angle absorption method (ABS) as well as the loading of the filter with black carbon as measured in accordance with VDI 2465, Sheet 1 is given in the following Table 1.

TABLE 1

|  | ATN | REF | ABS |
| --- | --- | --- | --- |
| n | 28 | 28 | 28 |
| $r^2$ | 0.62 | 0.89 | 0.91 |
| intercept | 0 | 17.3 ± 4.5 | 0 |
| slope | 7.2 ± 0.5 | 2.8 ± 0.2 | 3.3 ± 0.1 |

Further fields for industrial application are: continual black carbon mass concentration monitoring in the immission in environment networks, measuring black carbon emission in combustion processes (automotive engines, aircraft engines, firing systems), workplace monitoring, for example in factory buildings, on truck loading ramps, wharves;

ventilation monitoring, for example in factory buildings or in tunnel monitoring.

What is claimed is:

1. A method of optically measuring black carbon in the atmosphere, comprising the steps of:
    depositing aerosols from a stream of air onto a filter tape,
    illuminating an aerosol particle collection area of said filter tape continually by an illumination source with light of one or more wavelengths,
    measuring simultaneously light fractions both transmitted through and reflected from said filter tape at several precisely defined angles/angle ranges by means of photodetectors arranged correspondingly relative to said illumination source in achieving maximum symmetry for the angles to be measured, and
    determining continually the loading of said filter tape collection area with light-absorbing aerosol material from the change in the optical properties of said collection area caused by said loading with the aid of known algorithms from transmissivities and reflectivities as detected.

2. The method as set forth in claim 1 wherein said transmitted and reflected light fractions are measured at angles/angle ranges of 0°, 120 to 140° and 165 to 180° and then averaged.

3. The method as set forth in claim 1 wherein in measurement at a single wavelength only a narrow-band light source is employed.

4. The method as set forth in claim 3 wherein a color LED is used as said narrow-band light source.

5. The method as set forth in claim 1 wherein the light intensity of said illumination source is measured and determined continually.

6. An apparatus for implementing the method as set forth in claim 1 in the form of a measuring head comprising an illumination source arranged above a filter tape,
    a photodetector beneath said filter tape for measuring transmitted light fractions and photodetectors arranged between said illumination source and said filter tape for measuring reflected light fractions wherein, in each case, at least two of said photodetectors arranged between said illumination source and filter tape are provided opposite each other in ring-shaped mounting devices relative to said optical axis of said illumination source and are oriented at precisely defined angles/angle ranges θ of 0°, 120 to 140° and 165 to 180° relative to said filter tape surface, and units for determining the loading of said filter tape with light-absorbing material are arranged downstream to said photodetector beneath said filter tape and said photodetectors arranged opposite each other.

7. The apparatus as set forth in claim 6 wherein to reduce scattered light said photodetectors provided opposite each other are accommodated in two ring-shaped mounting devices located at two different planes.

8. The apparatus as set forth in claim 6 wherein a photodetector is provided for monitoring said light intensity of said illumination source.

9. The apparatus as set forth in claim 6 wherein in said measuring head a dusting passage is configured so that in addition to continual dusting of said filter tape also coarser particles (>10 μm) gain access to said filter tape.

* * * * *